United States Patent
Colman

(10) Patent No.: US 6,288,269 B1
(45) Date of Patent: Sep. 11, 2001

(54) APPARATUS FOR INTRODUCING FLUID INTO A PROCESS STREAM

(75) Inventor: Derek Alan Colman, Fleet (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/465,008

(22) Filed: Dec. 16, 1999

(30) Foreign Application Priority Data

Jan. 26, 1999 (GB) .................................................. 9901680

(51) Int. Cl.$^7$ ............................ C07C 67/055; F15D 1/02
(52) U.S. Cl. ......................... 560/245; 560/241; 137/802
(58) Field of Search .................... 560/245, 241; 137/802

(56) References Cited

U.S. PATENT DOCUMENTS

| | | |
|---|---|---|
| 2,925,331 | 2/1960 | Kazmierczak et al. . |
| 2,943,062 | 6/1960 | Mader . |
| 4,108,732 | 8/1978 | Nuttall, Jr. . |
| 4,126,539 | 11/1978 | Derr, Jr. et al. . |
| 4,188,490 * | 2/1980 | Hinnecamp et al. . |
| 4,409,396 | 10/1983 | Dempf et al. . |
| 4,471,821 | 9/1984 | Coulon et al. . |
| 4,654,801 * | 3/1987 | Stewart et al. . |
| 4,839,038 * | 6/1989 | McLain . |
| 4,902,484 | 2/1990 | Martin et al. . |
| 5,213,771 | 5/1993 | Hilliard et al. . |
| 5,440,039 | 8/1995 | Frosch et al. . |
| 5,579,588 * | 12/1996 | Reh et al. . |
| 6,013,834 * | 1/2000 | Colling . |

FOREIGN PATENT DOCUMENTS

| | | |
|---|---|---|
| 3731988 A1 | 5/1989 | (DE) . |
| 0 208 052 A2 | 1/1987 | (EP) . |
| 98/49125 | 11/1998 | (WO) . |

OTHER PUBLICATIONS

Derwent Abstract No. 1987–008763 [02], "Spinning medium intensely mixes with second medium—delivered to same end of reaction container".

Derwent Abstract No. 1989–107328 [15], "Reactor for catalytic processing of gases—has grid of rectangular, triangular or circular cross–section channels to produce more even flow to catalyser".

* cited by examiner

Primary Examiner—Paul J. Killos
Assistant Examiner—Robert W. Deemie
(74) Attorney, Agent, or Firm—Nixon & Vanderhye

(57) ABSTRACT

Apparatus for introducing a fluid into a process stream such as promoter into the feed stream of a reactor for manufacturing vinyl acetate comprises: (a) a process stream pipe having a bend and (b) a nozzle for introducing the fluid into the process stream downstream of the bend characterised in that the pipe has a flow-correction device downstream of the bend and the nozzle is mounted downstream of the flow-correction device to an end of a support arm which extends into the pipe in a direction substantially parallel to the direction of the pipe downstream of the bend.

13 Claims, 1 Drawing Sheet

APPARATUS FOR INTRODUCING FLUID INTO A PROCESS STREAM

The present invention relates to an apparatus for introducing a fluid into a process stream. In particular, though not exclusively, the present invention relates to an apparatus for introducing a fluid into a vinyl acetate reactor.

BACKGROUND OF THE INVENTION

Vinyl acetate may be produced by reacting acetic acid, oxygen and ethylene in the presence of a catalyst. The activity of the catalyst may be enhanced by using a promoter such as aqueous potassium acetate. Typically, the reaction is carried out in a fixed bed reactor containing the catalyst. A reactant process stream comprising acetic acid vapour, ethylene and oxygen is fed into the reactor through an inlet. The inlet comprises a pipe having a bend of an angle of between 45 to 90° upstream of the reactor. As reactant molecules flow past the bend in the pipe, they accelerate by varying amounts. This distorts the velocity distribution of the reactant molecules and, as a result, the velocity profile of the process stream is asymmetric.

The catalyst promoter is also introduced into the reactor through the pipe. Conventionally, this is achieved using a spray nozzle which is mounted to an end of a rigid support arm. The support arm is positioned downstream of the bend, and extends perpendicularly into the pipe from the pipe wall. The promoter is introduced into the pipe as liquid droplets from the nozzle; which partially evaporate whilst in the pipe. The promoter is carried by the reactant process stream into the reactor for distribution over the catalyst bed. However, because of the distorted velocity profile of the reactant process stream, the promoter is not deposited evenly over the catalyst. The problem is compounded by the support arm, which, by being configured at right angles to the direction of flow, further distorts the velocity profile of the reactant process stream.

BRIEF DESCRIPTION OF THE INVENTION

We have alleviated the problem by providing a new apparatus for introducing fluid into a process stream.

According to the present invention, there is provided apparatus for introducing a fluid into a process stream which apparatus comprises:

(a) a pipe for conducting said process stream, said pipe having a bend; and (b) a nozzle for introducing said fluid into said process stream downstream of said bend characterised in that said pipe has a flow-correction device downstream of said bend and said nozzle is mounted downstream of said flow-correction device to an end of a support arm which extends into said pipe in a direction substantially parallel to the direction of said pipe downstream of said bend.

The pipe bend may have an angle of 40 to 120° preferably, of about 45 to 100°. In a preferred embodiment, the pipe bend has an angle of about 90°.

In use, a process stream is fed into the pipe at a location upstream of the pipe bend. This process stream flows through the pipe, and past the pipe bend. Fluid is also introduced into the pipe through the nozzle. The nozzle fluid is introduced at a location downstream of the bend, and is carried along by the flow of the process stream. The nozzle is mounted on a support arm which extends into the interior of the pipe in a direction substantially parallel to the direction of the pipe downstream of the bend. Thus, the support arm causes minimal disturbance to the flow of process stream as it flows past the bend. Preferably, the support arm takes the form of a tube, which is coupled to a supply of nozzle fluid.

Preferably, the nozzle fluid is a liquid.

As the process stream flows past the bend, the molecules accelerate by varying amounts. This distorts the velocity distribution of the process stream and, as a result, the process stream velocity profile is non-uniformly asymmetric. The bend may also cause the process stream to swirl. At least one of these disadvantages may be alleviated by mounting a flow-correction device in the pipe of the present invention.

In one embodiment, the flow-correction device comprises a body having a plurality of longitudinal channels. In use, the body is positioned downstream of the pipe bend and configured such that the channels are substantially parallel with the direction (longitudinal axis) of the pipe downstream of the bend. As the process stream flows through the channels, any swirl in the flow pattern is reduced. The velocity distribution of the process stream, however, remains unchanged.

In a preferred embodiment of the invention, the flow-correction device comprises a plate having perforations. The perforations may take the form of pores or apertures which, preferably, are evenly spaced apart from one another. For example, the plate may comprise a plurality of holes with diameters of 5 to 30 mm, preferably, 8 to 12 mm. These holes may be spaced apart by about 5 to 30 mm, preferably, 12 to 17 mm. In a preferred embodiment, the plate has a plurality of 10 mm diameter holes spaced 14.7 mm apart. In use, the plate reduces the free area of flow through the pipe such that process stream passing through the perforations experiences a drop in pressure. The pressure drop may be equivalent to about 5 to 20 velocity heads based on the pipe inlet flow. The pressure drop causes an increase in turbulence and a near equal flux through the holes of the plate. As a result, distortions in the velocity profile of the process stream are reduced or eliminated.

The nozzle is positioned downstream of the flow-correction device. Thus, the nozzle fluid introduced into the pipe is carried along the pipe by a flow of process stream whose flow pattern has been corrected either for swirling and/or non-uniformity in the velocity distribution profile.

Where a plate having perforations is employed as a flow-correction device, the nozzle may be coupled to the plate. In one embodiment, the plate having perforations is provided with a hole. In use, the nozzle is inserted through the hole and held in place, for example, by retaining means. The retaining means may take the form of a guide sleeve which is coupled to the plate. The guide sleeve can be used to ensure that the nozzle is placed in the same position every time it is used. Preferably, the guide sleeve ensures that the tip of the nozzle just protrudes from the underside of the plate. This allows nozzle fluid to be introduced into the optimum mixing zone of the pipe.

The present invention may be employed as an inlet for a fixed bed reactor, for example, to contact process stream and nozzle fluid with a catalyst bed positioned therein. In one embodiment, the present inlet is coupled to a fixed bed reactor for the production of vinyl acetate. In this embodiment, a process stream comprising acetic acid vapour, ethylene and oxygen is fed into the reactor, whilst a promoter of, for example, potassium acetate solution, is introduced into the reactor as a nozzle fluid. The promoter may evaporate on entering the pipe and is carried by the flow of reactants into the reactor for deposition over the catalyst bed. It has been found that fluid deposits more evenly over the catalyst bed as a vapour rather than a liquid. Thus, in a preferred embodiment, the distance between the nozzle and catalyst bed is adjusted to maximise the residence time of the nozzle fluid in the inlet. This ensures that the a relatively large proportion of the nozzle fluid is evaporated before entering the reactor.

The present invention may further comprise a distributor, for example, in the form of a plate. The plate is preferably circular and, when mounted over a portion of a catalyst bed, provides a bluff surface which is substantially perpendicular to the direction of the pipe downstream of the bend. The plate removes some of the dynamic pressure of the incoming process stream/nozzle fluid mixture through turbulent eddies and promotes back-mixing of the process stream/nozzle fluid mixture by setting up recirculation within the reactor head-space. This ensures that the nozzle fluid is adequately dispersed in the process fluid, and can be deposited onto the catalyst bed in an even manner. The plate may be mounted on support members which may be secured to the surface of the catalyst bed, for example, by embedding the members to a predetermined depth beneath the surface of the catalyst bed. Preferably, the plate is mounted over a central region of the catalyst bed.

According to a further aspect of the present invention, there is provided a process for the production of vinyl acetate in a fixed bed reactor, said process comprising the steps of:

providing a pipe having a bend and a flow-correction device downstream of said bend, coupling the pipe to a fixed bed reactor, providing a nozzle which is mounted to an end of a support arm, positioning the nozzle in the pipe such that the nozzle is located downstream of the bend and downstream of the flow-correction device, and the support arm extends into the pipe in a direction substantially parallel to the direction of the pipe downstream of the bend, feeding a reactant process stream comprising acetic acid, ethylene and oxygen into the reactor along the pipe, feeding a catalyst promoter fluid into the reactant process stream through the nozzle to deposit the promoter over the catalyst bed, and reacting the ethylene, acetic acid and oxygen containing gas in the reactor to produce vinyl acetate.

BRIEF DESCRIPTION OF THE DRAWING

These and other aspects of the present invention will now be described, by way of example, with reference to FIG. 1 which is a schematic view of apparatus for introducing a fluid into a process stream in accordance with an embodiment of the present invention.

DETAILED DESCRIPTION OF PREFERRED EMBODIMENTS

Figure 1:
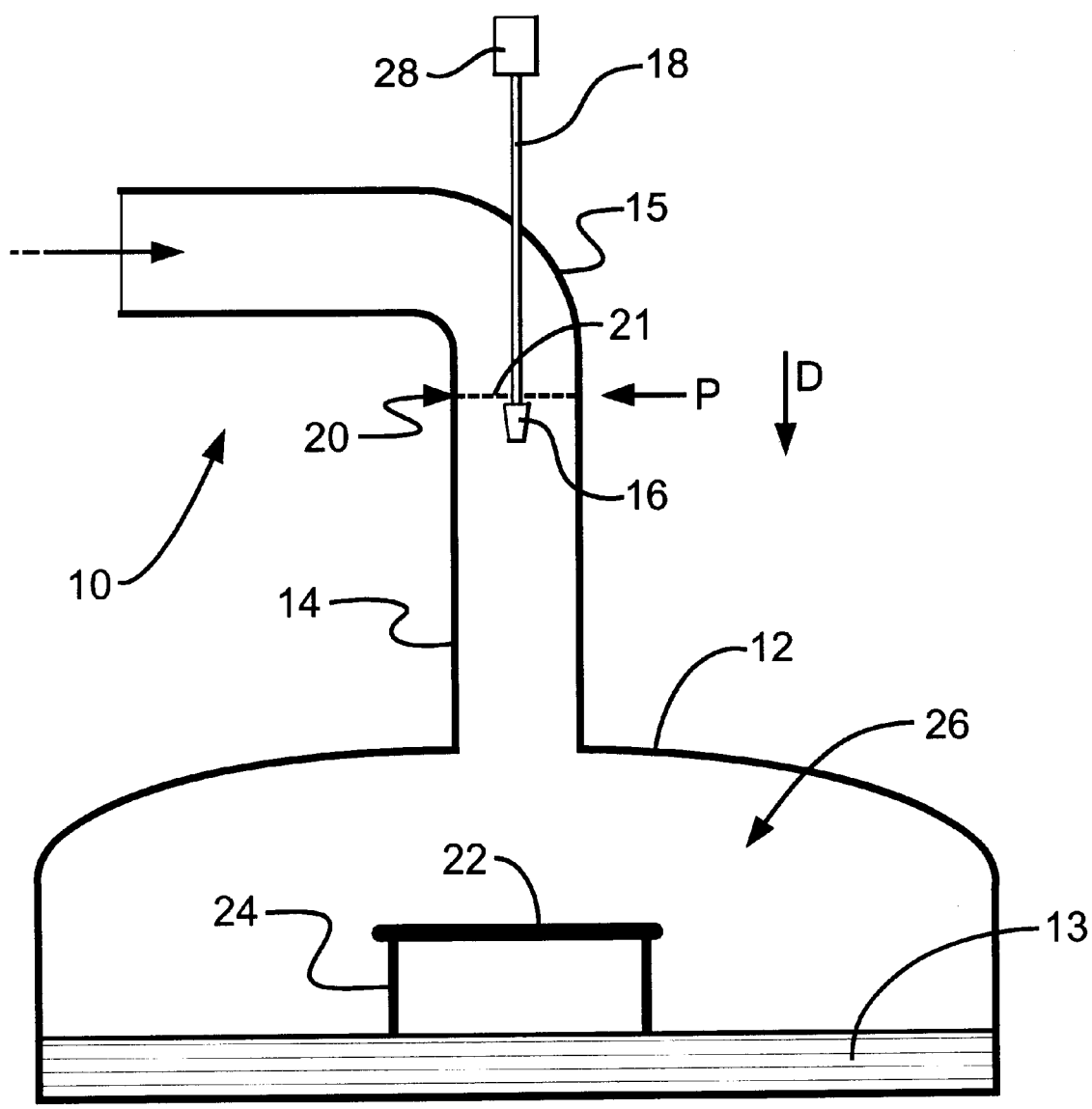

In FIG. 1, an inlet (10) is shown mounted to a fixed bed reactor (12) which houses a catalyst bed (13). The inlet (10) comprises a pipe (14), a spray nozzle (16), a support arm (18) and flow-correction device (20). The pipe (14) has a bend (15) of an angle of about 90° upstream of the reactor (12). The nozzle (16) is located downstream of the bend, and is mounted to an end of the support arm (18) which is a tube coupled to a supply (28) of nozzle fluid. As shown in the drawing, the support arm (18) extends into the pipe (14) in a direction "D" which is parallel to the direction of the pipe (14) downstream of the bend(15).

In use, a reactant process stream comprising acetic acid vapour, ethylene and oxygen is introduced into the reactor (12) via the pipe (14). As the process stream travels round the bend (15), the reactant molecules accelerate by varying amounts. This distorts the velocity profile of the stream. The velocity profile is subsequently corrected using the flow-correction device (20).

The flow-correction device (20) comprises a perforate plate which is mounted to the pipe (14) at position "P". The plate comprises a plurality of 10 mm diameter holes (21) which are spaced apart from one another by 14.7 mm. In use, the plate reduces the free area of flow through the pipe such that process stream passing through the perforations experiences a drop in pressure. This causes an increase in turbulence, and a near equal flux through the perforations. As a result, distortions in the velocity profile of the stream are reduced or eliminated.

A promoter of potassium acetate solution is introduced into the process stream in the pipe (14) using the spray nozzle (16), and is carried into the reactor (12) by the "corrected" flow of reactants. The nozzle (16) is inserted in a hole in the perforate plate such that the tip of the nozzle just protrudes from the underside of the plate. The nozzle (16) is held in this position by a guide sleeve (not shown).

On entering the reactor (12), at least a portion of the promoter/reactant stream comes into contact with a distributor (22). The distributor (22) takes the form of a plate which is mounted over the catalyst bed (13) on support members (24). The plate provides a bluff surface substantially perpendicular to the direction "D". Thus, when fluid comes into contact with the plate, some of the dynamic pressure of the incoming fluid is removed through turbulent eddies. This promotes back-mixing of the reactant/promoter mixture in the reactor head-space (26), ensuring that the promoter is fully dispersed in the reactant stream. The homogenous reactant/promoter mixture can thus be used to deposit the promoter evenly over the catalyst bed (13).

What is claimed is:

1. A process for the production of vinyl acetate in a fixed bed reactor, said process comprising the steps of:

(i) providing a pipe having a bend and a flow-correction device downstream of said bend, (ii) coupling the pipe to a fixed bed reactor comprising a reactor bed, (iii) providing a nozzle which is mounted to an end of a support arm, (iv) positioning said nozzle in said pipe such that said nozzle is located downstream of said bend and downstream of said flow-correction device, and said support arm extends into said pipe in a direction substantially parallel to the direction of said pipe downstream of said bend, (v) feeding a reactant process stream comprising acetic acid, ethylene and oxygen into said reactor along said pipe, (vi) feeding a catalyst promoter fluid into said reactant process stream through said nozzle to deposit said promoter over said catalyst bed, and (vii) reacting said ethylene, acetic acid and oxygen containing gas in said reactor to produce vinyl acetate.

2. A process as claimed in claim 1, wherein said fixed bed reactor comprises a fixed bed reactor comprising a catalyst bed having an inlet for a process stream comprising acetic acid vapor, ethylene and an oxygen-containing gas for a nozzle fluid comprising potassium acetate solution, said inlet comprising a pipe for conducting said process stream, said pipe having a bend, and a nozzle for introducing said fluid into said process stream downstream of said bend, said pipe having a flow-correction device downstream of said bend and said nozzle being mounted downstream of said flow-correction device to an end of a support arm which extends to said pipe in a direction substantially parallel to the direction of said pipe downstream of said bend.

3. A process as claimed in claim 2 wherein, in said fixed bed reactor, there is mounted a distributor plate over a portion of the catalyst bed substantially perpendicular to the direction of the pipe downstream of the bend.

4. A process as claimed in claim 1 wherein said fixed bed reactor comprises a catalyst bed therein having an inlet for a process stream comprising acetic acid vapor, ethylene and an oxygen-containing gas and for a nozzle fluid comprising potassium acetate solution, said inlet comprising a pipe for conducting said process stream, said pipe having a bend, and a nozzle for introducing said fluid into said process stream downstream of said bend, said pipe having a flow-correction device comprising a plate having perforations downstream of said bend, said nozzle being mounted downstream of said flow-correction device to an end of a support arm which extends into said pipe in a direction substantially parallel to the direction of said pipe downstream of said bend.

5. A process as claimed in claim in 1 in which said pipe bend has an angle of about 40 to 120°.

6. A process as claimed in claim in 5 in which said pipe bend has an angle of about 45 to 100°.

7. A process as claimed in claim in 6 in which said pipe bend has an angle of about 90°.

8. A process as claimed in claim in 3 in which said pipe bend has an angle of about 40 to 120°.

9. A process as claimed in claim in 8 in which said pipe bend has an angle of about 45 to 100°.

10. A process as claimed in claim in 9 in which said pipe bend has an angle of about 90°.

11. A process as claimed in claim in 4 in which said pipe bend has an angle of about 40 to 120°.

12. A process as claimed in claim in 11 in which said pipe bend has an angle of about 45 to 100°.

13. A process as claimed in claim in 12 in which said pipe bend has an angle of about 90°.

* * * * *